US006001816A

United States Patent [19]
Morsy et al.

[11] Patent Number: 6,001,816
[45] Date of Patent: Dec. 14, 1999

[54] GENE THERAPY FOR LEPTIN DEFICIENCY

[75] Inventors: Manal A. Morsy, Blue Bell; Ming Cheng Gu; Jing Zhoa, both of Lansdale, all of Pa.; C. Thomas Caskey, Houston, Tex.

[73] Assignee: Merck & Co., Inc., Rahway, N.J.

[21] Appl. No.: 08/878,738

[22] Filed: Jun. 19, 1997

Related U.S. Application Data

[60] Provisional application No. 60/020,812, Jun. 20, 1996.
[51] Int. Cl.$^6$ .................................................... A01N 43/04
[52] U.S. Cl. ........................... 514/44; 514/44; 435/320.1; 435/325
[58] Field of Search ........................... 514/44; 435/320.1, 435/325

[56] References Cited

U.S. PATENT DOCUMENTS

| | | | |
|---|---|---|---|
| 5,401,629 | 3/1995 | Harpold et al. | 435/69.1 |
| 5,436,128 | 7/1995 | Harpold et al. | 435/6 |
| 5,643,748 | 7/1997 | Snodgrass et al. | 435/6 |

FOREIGN PATENT DOCUMENTS

| | | |
|---|---|---|
| 2104996 | 1/1994 | Canada . |
| 0 736 599 A2 | 10/1996 | European Pat. Off. . |
| 0 741 187 A2 | 11/1996 | European Pat. Off. . |
| 0 743 321 A2 | 11/1996 | European Pat. Off. . |
| 0 744 408 A2 | 11/1996 | European Pat. Off. . |
| 2292382 | 2/1996 | United Kingdom . |
| WO 92/02639 | 2/1992 | WIPO . |
| WO 92/07943 | 5/1992 | WIPO . |
| WO 96/05309 | 2/1996 | WIPO . |
| WO 96/08510 | 3/1996 | WIPO . |
| WO 96/24670 | 8/1996 | WIPO . |
| WO 96/35787 | 11/1996 | WIPO . |
| WO 96/36644 | 11/1996 | WIPO . |
| WO 96/37517 | 11/1996 | WIPO . |
| WO 96/38586 | 12/1996 | WIPO . |
| WO 97/02004 | 1/1997 | WIPO . |
| WO 97/02048 | 1/1997 | WIPO . |
| WO 97/19952 | 6/1997 | WIPO . |
| WO 97/32022 | 9/1997 | WIPO . |

OTHER PUBLICATIONS

Feldman et al., Fundamental & Clinical Pharmacology, 1995.
Ross et al. Human Gene Therapy, vol. 7, pp. 1781–1790, Sep. 1996.
Verma et al. Nature, vol. 389, pp. 239–242, Sep. 18, 1997.
Morsy et al. Proc. Natl. Acad. Sci., USA, vol. 95, pp. 7866–7871, 1998.
Clayton et al. Arch Dis Child, vol. 78, 278–284, 1998.
Fletcher et al. Blood, vol. 86, p. 241a, Nov. 15, 1995.
Tartaglia et al. Cell, vol. 83, pp. 1263–1271, 1995.
Spady, DK et al. J. Clin. Invest., vol. 96, pp. 700–709, Aug. 1995.
Murakami, T. et al. Biochem. and Biophysical Res. Comm., vol. 209, pp. 944–952, Apr. 26, 1995.
Andersson et al. "Cloning, structure, and expression of the mitochondrial cytochrome P–450 sterol 26–hydroxylase, a bile acid biosynthetic enzyme," 1989 J. Biol. Chem. 264:8222–8229.
Barnes, W.M. "PCR amplification of up to 35–Kb DNA with high–fidelity and high–yield from lambda–bacteriophage," 1994 Proc. Natl. Acad. Sci. 91:2216–2220.
Baumann et al. "The full–length leptin receptor has signalling capabilities of interleukin 6–type cytokine receptors" 1996 Proc. Natl. Acad. Sci. USA 93:8374–8378.
Campfield et al. "Recombinant Mouse OB Protein: Evidence for a Peripheral Signal Linking Adiposity and Central Neural Networks", 1995 Science 269:546–549.
Chehab et al. "Correction of the sterility defect in homozygous obese female mice by treatment with the human recombinant leptin", 1996 Nature Genetics 12:318–320.
Chen et al. "Evidence that the diabetes gene encodes the leptin receptor: Identification of a mutation in the leptin receptor gene in db/db mice" 1996 Cell 84:491–495.
Chen et al. "Disappearance of body fat in normal rats induced by adenovirus–mediated leptin gene therapy", 1996 Proc. Natl. Acad. Sci., USA 93:14795–14799.
Chen et al. "Production and Characterization of Human 293 Cell Lines Expressing the Site–Specific Recombinase Cre", 1996 Somatic Cell & Mol. Genet. 22:477–488.
Chen et al. "Persistence in muscle of an adenoviral vector that lacks all viral genes", 1997 Proc. Natl. Acad. Sci. USA 94:965–972.
Chua et al. "Phenotypes of mouse diabetes and rat fatty due to mutations in the OB (leptin) receptor", 1996 Science 271:994–996.
Chua et al. "Phenotype of fatty due to Gin269Pro mutation in the leptin receptor (Lepr)", 1996 Diabetes 45:1141–1143.
Cioffi et al. "Novel B219/OB receptor isoforms:Possible role of leptin in hematopoiesis and reproduction", 1996 Nature Medicine 2:585–588.
Clark et al. "The Diabetic Zucker Fatty Rat (41611)", 1983 Proc. Soc. Exp. Biol. Med. 173:68–75.
Clemens et al. "In vivo muscle gene transfer of full–length dystrophin with an adenoviral vector that lacks all viral genes", 1996 Gene Ther. 3:965–972.
Fisher et al. "Recombinant adenovirus deleted of all viral genes for gene therapy of cystic fibrosis", 1996 Virology 217:11–22.
Fletcher et al. "Replacement gene therapy phenotypically corrects the fat deposition defect in ob/ob mice", 1995 Blood 86(10), Supp.1: p. 241a (abstract 951).

(List continued on next page.)

*Primary Examiner*—Brian H. Stanton
*Assistant Examiner*—Michael C. Wilson
*Attorney, Agent, or Firm*—Anna L. Cocuzzo; Joanne M. Giesser; Jack L. Treibble

[57] ABSTRACT

Gene therapy can treat obesity in mammals. An adenoviral vector encoding a leptin gene is delivered intravenously to a mammal with a deficiency in functional leptin to decrease weight, decrease serum insulin levels or decrease serum glucose levels.

3 Claims, 8 Drawing Sheets

OTHER PUBLICATIONS

Flier et al. "Obesity research springs a proton leak", 1997 Nature Genetics 15:223–224.

Ghilardi et al. "Defective STAT signaling by the leptin receptor in diabetic mice" 1996 Proc. Natl. Acad. Sci. USA 93:6231–6235.

Guan et al. "Differential expression of mRNA for leptin receptor isoforms in the rat brain", 1997 Molec. and Cell. Endocrinology, 133:1–7.

Haecker et al."In Vivo Expression of Full–Length Human Dystrophin from Adenoviral Vectors Deleted of All Viral Genes", 1996 Hum. Gene. Ther. 7:1907–1914.

Halaas et la. "Weight–reducing effects of the plasma–protein encoded by the obese gene", 1995 Science 269:543–546.

Hardy et al. "Construction of adenovirus vectors through Cre–lox recombination", 1997 J. Virol 71:1842–1849.

Hodgson, J. "Receptor screening and the search for new pharmaceuticals" 1992 Bio/Technology 10:973–977.

Ilda et al. "Phenotype–linked amino acid alteration in leptin receptor cDNA from zucker fatty (fa/fa) rat" 1996 Biochem. Biophys. Res. Comm. 222:19–26.

Kochanek et al. "A new adenoviral vector: Replacement of all viral coding sequences with 28 kb of DNA independently expressing both full–length dystrophin and beta–galactosidase", 1996 Proc. Natl. Acad. Sci. USA 93:5731–5736.

Kumar–Singh and Chamberlain "Encapsidated adenovirus minichromosomes allow delivery and expression of a 14 kb dystrophin cDNA to muscle cells", 1996 Hum. Mol. Genet. 5:913–921.

Lee et al. "Abnormal splicing of the leptin receptor in diabetic mice", 1996 Nature 379:632–635.

Lieber et al. "Recombinant adenoviruses with large deletions generated by Cre–mediated excision different biological properties compared with first–generation vectors in vitro and in vivo" 1996 J. Virol. 70:8944–8960.

McKnight et al. "Transcriptional control signals of a eukaryotic protein–coding gene", 1982 Science 217:316–324.

Mellon et al. "Immortalization of hypothalamic GnRH neurons by genetically targeted tumorigenesis", 1990 Neuron 5:1–10.

Mitani et al. "Rescue, propagation, and partial purification of a helper virus–dependent adenovirus vector" 1995 Proc. Natl. Acad. Sci. USA 92:3854–3858.

Morgan et al. "Human gene therapy" 1993 Ann. Rev. of Biochem. 62:191–217.

Murakami et al. "Cloning of rat obese cDNA and its expression in obese rats", 1995 Biochem. and Biophys. Res. Comm. 209(3):944–952.

Muzzin et al. "Correction of obesity and diabetes in genetically obese mice by leptin gene therapy", 1996 Proc. Natl. Acad. Sci. USA 93:14804–14808.

Parks & Graham "A helper–dependent system for adenovirus vector production helps define a lower limit for efficient DNA packaging", 1997 J. Virol. 71:3293–3298.

Parks et al. "A helper–dependent adenoviral system: removal of helper virus by Cre–mediated excision of the viral packaging signal", 1996 Proc. Natl. Acad. Sci. 93:13565–13570.

Pellymounter et al. "Effects of the obese Gene Product on Body Weight Regulation in ob/ob Mice", 1995 Science 269:540–543.

Phillips et al. "Leptin receptor missense mutation in the fatty zucker rat", 1996 Nature Genetics 13:18–19.

Pine et al. "Tyrosine–phosphorylated p91 binds to a single–element in the isgf2/irf–1 promoter to mediate induction by ifn–alpha and ifn–gamma, and is likely to autoregulate the p91 gene", 1994 Embo Journal 13:158–167.

Rentsch et al. "Recombinant OB–gene product reduces food intake in fasted mice", 1995 Biochem. and Biophys. Res. Comm. 214(1):131–136.

Rosenblum et al. "Functional STAT 1 and 3 signaling by the leptin receptor (OB–R); reduced expression of the rat fatty leptin receptor in transfected cells," 1996 Endocrinology 137(11):5178–5181.

Schadlow et al. "Regulation of gene expression in PC12 cells via an activator of dual second messengers: pituitary adenylate cyclase activating polypeptide" 1992 Mol. Biol. Cell 3:941–951.

Sims et al. "A novel interferon–inducible domain—structural and functional—analysis of the human interferon regulatory factor–I gene promoter", 1993 Molecular And Cellular Biology 13:690–702.

Spiegelman et al. "Adipogenesis and Obesity: Rounding out the big picture", 1996 Cell 87:377–389.

Stephens et al. "The role of neuropeptide Y in the atiobesity action of the obese gene product", 1995 Nature 377:530–532.

Takaya et al. "Molecular cloning of rat leptin receptor isoform complementary DNAs—identification of a missense mutation in Zucker fatty (fa/fa) rats", 1996 Biochem. Biophys. Res. Comm. 225:75–83.

Tartaglia et al. "Identification and expression cloning of a leptin receptor, ob–r", 1995 Cell 83:1263–1271.

Truett et al. "Rat obesity gene fatty (fa) maps to chromosome 5: Evidence for homology with the mouse gene diabetes (db)", 1991 Proc. Natl. Acad. Sci. USA 88:7806–7809.

Wang et al., "A novel leptin receptor isoform in rat", 1996 FEBS Letters 392:87–90.

Wiegle et al. "Recombinant ob Protein Reduces Feeding and Body Weight in the ob/ob Mouse" 1995 J. Clin. Invest. 96:2065–2070.

Zhang et al. "Positional cloning of the mouse obese gene and its human homolog", 1994 Nature 372:425–432.

Zhong et al. "Stat–3 a stat family member activated by tyrosine phosphorylation in response to epidermal growth–factor and interleukin–6", 1994 Science 264:95–98.

Zucker and Zucker "Fat accretion and growth in the rat", 1963 J. Nutrition 80:6–19.

Zucker and Zucker "Heredity obesity in the rat associated with high serum fat and cholesterol", 1962 Proc. Soc. Exp. Miol. Med. 110:165–171.

Zucker and Zucker "Fatty, a new mutation in the rat", 1961 J. Heredity 52:275–278.

GENE THERAPY FOR LEPTIN DEFICIENCY

CROSS-REFERENCE TO RELATED APPLICATIONS

This applicatiion claims priority to provisional application 60/020,812 filed Jun. 20, 1996.

STATEMENT REGARDING FEDERALLY-SPONSORED R&D

Not Applicable

REFERENCE TO MICROFICHE APPENDIX

Not Applicable

FIELD OF THE INVENTION

This invention relates to methods of gene therapy for obesity. This invention also relates to vectors useful in this gene therapy.

BACKGROUND OF THE INVENTION

Leptin is a protein expressed by the ob gene. Leptin is secreted by adipose tissue and appears to be both a satiety factor and a regulator of metabolism (Levin et al., 1996 *Proc. Natl Acad. Sci. USA* 93:1726–1730). Both the mouse gene and its human homologue have recently been identified and sequenced (Zhang et al., 1994 *Nature* (London) 372:425–431.)

Mice which are homozygous for the ob gene (ob/ob) are obese, perhaps due to an underexpression of leptin. When ob/ob mice are given daily injections of recombinant protein, their food intake was markedly inhibited and they experienced a reduction in body weight and fat. In lean (i.e. wild-type) mice, daily injections of leptin lead to modest decreases of food intake and body weight. The results for body fat have been contradictory. (Pelleymounter et al., 1995, *Science* 269:540–543; Halaas et al., 1995 *Science* 269: 543–546; and Campfield et al., 1995 *Science* 269:546–549.

Obesity in humans is a major disorder associated with mortality, and may result from a number of causes, and at least some may be due to an insufficient amount of leptin produced. Since leptin is a protein, and vulnerable to breakdown and inactivation by the gastrointestinal system, it cannot be delivered orally. It would be desirable to develop a therapy for leptin delivery for obese patients whose obesity is due, in part to a paucity of leptin.

Some forms of obesity do not appear to be treatable by the administration of leptin. In these cases, it is possible that the problem may be due to an insufficient amount of leptin receptors on the cell surface. Alternatively, the receptors which are present on the cell surface may contain mutations which do not allow them to bind to leptin efficiently or efficiently process the signal generated by the leptin binding. Currently no therapy exists which could augment or replace these receptors.

SUMMARY OF THE INVENTION

Not Applicable

BRIEF DESCRIPTION OF THE INVENTION

This invention is related to gene therapy for obesity. One aspect of this invention involves a method of treating obesity, lowering serum glucose levels or lowering serum insulin levels in a mammal in need of such therapy comprising delivering a gene encoding an obesity regulating gene to said mammal; and allowing sufficient time to pass for transcription and translation of the obesity regulating gene.

Some types of obesity are caused by an insufficient amount of leptin or an insufficient amount of functional leptin receptors present on the cell surface. Thus, another aspect of this invention is a method of treating obesity comprising delivering a gene encoding leptin or a leptin receptor to a mammal; and allowing sufficient time to pass for transcription and translation of the leptin or leptin receptor gene. A specific embodiment of this invention is gene therapy for a mammal whose obesity, elevated level of serum glucose or elevated level of insulin in due, at least in part to an insufficient amount of leptin produced. By "insufficient amount of leptin produced" it is envisioned that the animal may produce functional leptin, but at lower levels than required; a complete inability to produce leptin; or production of a mutated form of leptin which either fuctions less efficienly than native leptin or does not function at all. Thus, this invention is directed to a method of treating obesity, an elevated level of serum glucose or an elevated insulin, which is, at least in part, due to an insufficient amount of leptin produced by a mammal comprising: delivering a gene encoding leptin to the mammal and allowing suffient time to pass for transcription and translation of the leptin gene.

Obesity may occur in an animal which is producing normal quantities of leptin, but whose leptin receptors are either not able to bind and process the leptin properly, or have not been produced in sufficient quantity. These situations may be remedied by gene therapy using a leptin receptor. Thus another aspect of this invention is a treatment for obesity, excess plasma insulin levels or excess plasma glucose levels, any of which are a result, at least in part, of an insufficient amount of functional leptin receptor production by a mammal. Thus, one aspect of this invention is a method of increasing the amount of leptin receptors in a mammal comprising: delivering a gene encoding a leptin receptor to the mammal, and allowing sufficient time to pass for transcription and translation of the leptin receptor gene.

As used throughout the specification and claims, the following definitions apply:

"Native" a gene or protein is native if it naturally occurs in a given organism.

"Leptin gene": a gene from any mammal which encodes a native leptin, or a derivative thereof. A "derivative" is a modified leptin molecule which retains at least 80% of the biological activity of native leptin.

"Leptin receptor": a gene from any mammal which encodes a native leptin receptor, or a derivative thereof. A "derivative" is a modified receptor molecule which binds native leptin at least 80% as efficiently as a native receptor molecule.

"Obesity regulating gene": a gene whose gene product is involved in the regulation of obesity in a mammal, including genes encoding leptin, leptin receptors, neuropeptide Y, and the like.

In the past, recombinant leptin has been administered to animals who exhibiting an obese phenotype, and a daily injection has been shown to decrease body weight. There are numerous disadvantages to this method of treating obesity, however. First, this method is helpful only for those animals whose obesity is caused, at least in part by an insufficient amount of leptin produced. Not all obesity is due to this defect. Further, injections are not a particularly convenient method of treatment, particularly for long-term treatments. In addition, the half-life of leptin is short, so the duration of the treatment was found to be only about 24 hours, after which the animals were observed to regain weight.

This invention solves the problems associated with a daily administration of recombinant protein by providing a vector which can express leptin or a leptin receptor in vivo. It has been surprisingly found that leptin which is expressed in vivo is more advantageous than administration of recombinant leptin; its effects last longer, and most surprisingly, is up to 20 fold more potent than recombinant leptin administered by injection.

Expression of a leptin receptor or neuropeptide Y in vivo allows for treatment of heretofore untreatable types of obesity.

Genes

The sequences of leptin and leptin genes from various species are known (Zhang et al., 1994 *Nature* 372:425; Ogawa et al., 1995 *J. Clin. Invest.* 96:1647–1652; Murakami et al., 1995 *Biochem. Biophys. Res. Commun.* 209:944; and Considine et al., 1995 *J. Clin. Invest.* 95:2986; each of which is hereby incorporated by reference). If desired, genes encoding leptin derivatives may also be used. Since the amino acid and nucleotide sequence of leptin is known, it is well within the skill of one of the ordinary artisian to construct a nucleotide sequence which encodes a desired mutant form of leptin. These can be used to study structure and function relationships involved in leptin binding and signaling in the transgenic animal model.

The amino acid sequences of leptin receptors and the nucleic acid sequences of genes encoding leptin receptors are also known; see, for example Toriaglla et al., 1995, *Cell* 83:1–20 which is hereby incorporated by reference. The leptin receptors can exist in various isoforms, due to alternate splicing. The biological consequences of the presence of many of these isoforms is not clearly understood. However, a mutation that results in premature termination of the long form of the mouse leptin receptor is apparently responsible for the obese phenotype of the db/db mouse (Lee et al., 1996, *Nature* 379:632–635; Chua et al., 1996, *Science* 271:994–996; and Chen et al., 1996, *Cell* 84:491–495).

In further aspects of this invention, a derivative leptin receptor is introduced into a mammal, and the resulting mammal can be used to study structure and functional relationships between leptin binding and the leptin receptor.

The gene which encodes the leptin or leptin receptor should also contain at least one element which allows for expression of the gene when introduced into the host cell environment. These sequences include, but are not limited to promoters, response elements, and enhancer elements. In a preferred aspect of this invention, promoters are chosen which are regulatable; i.e. are inducible rather than constitutive. Particular examples of such promoters include: Sr-alpha, CMV, regulatable tet, P-450, albumin and the like.

Vector

The heterologous leptin or lepin receptor gene may be delivered to the organism using a vector or other delivery vehicle. DNA delivery vehicles can include viral vectors such as adenoviruses, adeno-associated viruses, and retroviral vectors. See, for example: Chu et al. 1994 *Gene Ther* 1: 292–299; Couture et al. 1994 *Hum Gene Ther* 5:667–677; and Eiverhand et al. 1995 *Gene Ther* 2: 336–343. Non-viral vectors which are also suitable include DNA-lipid complexes, for example liposome-mediated or ligand/poly-L-Lysine conjugates, such as asialoglyco-protein-mediated delivery systems. See, for example: Feigner et al. 1994 *J. Biol. Chem*, 269: 2550–2561; Derossi et al. 1995, *Restor. Neurol. Neuros.* 8: 7–10; and Abcallah et al. 1995 *Biol. Cell* 85: 1–7.

If a vector is chosen as the delivery vehicle for the obesity regulating gene, it may be any vector which allows expression of the gene in the host cells. It is preferable if the vector also is one which is capable of integrating into the host genome, so that the gene can be expressed permanently, but this is not required. In cases where the vector does not integrate into the host genome, the expression of the gene may be transient rather than permanent.

One vector which is suitable for transient expression of the ob gene is an adenovirus which has a deletion in the El gene. Such vectors are known, as taught in the aforementioned WO 95/00655 and Mitani et al., 1995 publications. These viruses preferentially infect hepatocytes, where they persist for approximately 3–4 weeks after the initial infection. While in the hepatocytes, these viruses can express the heterologous gene.

The vector is administered to the host, generally by IV injection. Suitable titers will depend on a number of factors, such as the particular vector chosen, the host, strength of promoter used and the severity of the disease being treated. For mice, an adenovirus vector is preferably administered as an injection at a dose range of from about $5.0 \times 10^6$ to about $10 \times 10^6$ plaque forming units (PFU) per gram body weight. Preferred dosages range from at least about $6-9 \times 10^6$ PFU/gm body weight, and more preferred is from at least about $6.7-8.6 \times 10^6$ PFU/gm body weight (equivalent to approximately at least $1-5 \times 10^8$ PFU for mice).

Thus this invention specifically is directed to a method of treating obesity, elevated serum glucose levels or elevated insulin levels which is, at least in part, due to an insufficient amount of leptin or leptin receptors by a mammal comprising:

a) transfecting the mammal with a viral vector comprising a gene encoding leptin or leptin receptors; wherein said vector further comprises at least one element regulating its expression in a mammalian tissue; and b) allowing sufficient time to pass for transcription and translation of the leptin gene.

Hosts

Animals which transiently express the ob or ob-receptor gene products are valuable research tools. For example, they can be used to monitor the effects of decreasing amounts of leptin, or the effect of various exogenously supplied substances (such as hormones or putative leptin receptor agonists and antagonists) in an environment of decreasing leptin availability.

Aside from making animal models useful in studying various aspects of obesity, this invention is specifically directed to gene therapy for humans.

In accordance with this invention, mice which are obese (ob/ob) have been injected with an adenovirus containing the human leptin gene, although the leptin gene from any desired species may be used, and in preferred embodiments, the gene which is from the same species as the host is used. These were compared with ob/ob mice injected with an adenovirus containing only a marker gene (β-galactosidase), those receiving injections of recombinant leptin, and to untreated controls. Further controls used in some of the experiments are db/db mice (obese, but unresponsive to leptin injections).

Figure 1:
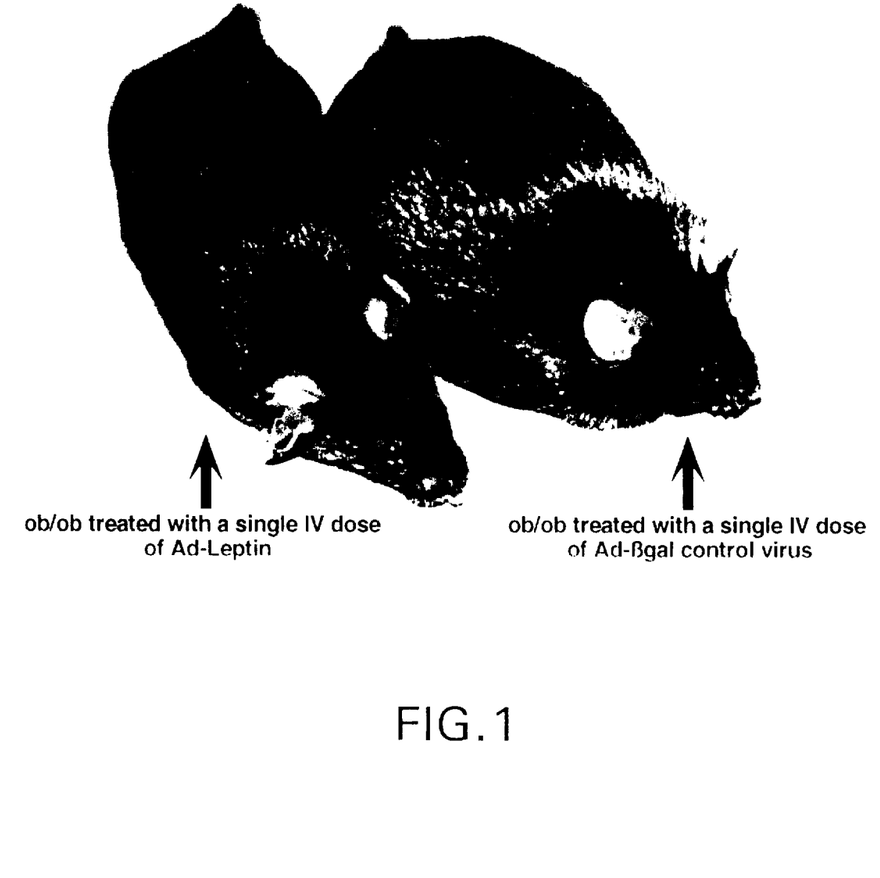
FIG. 1 is a photograph of two ob/ob mice. The mouse on the right is from a control group. The mouse on the left received gene therapy in accordance with this invention.
Figure 2:
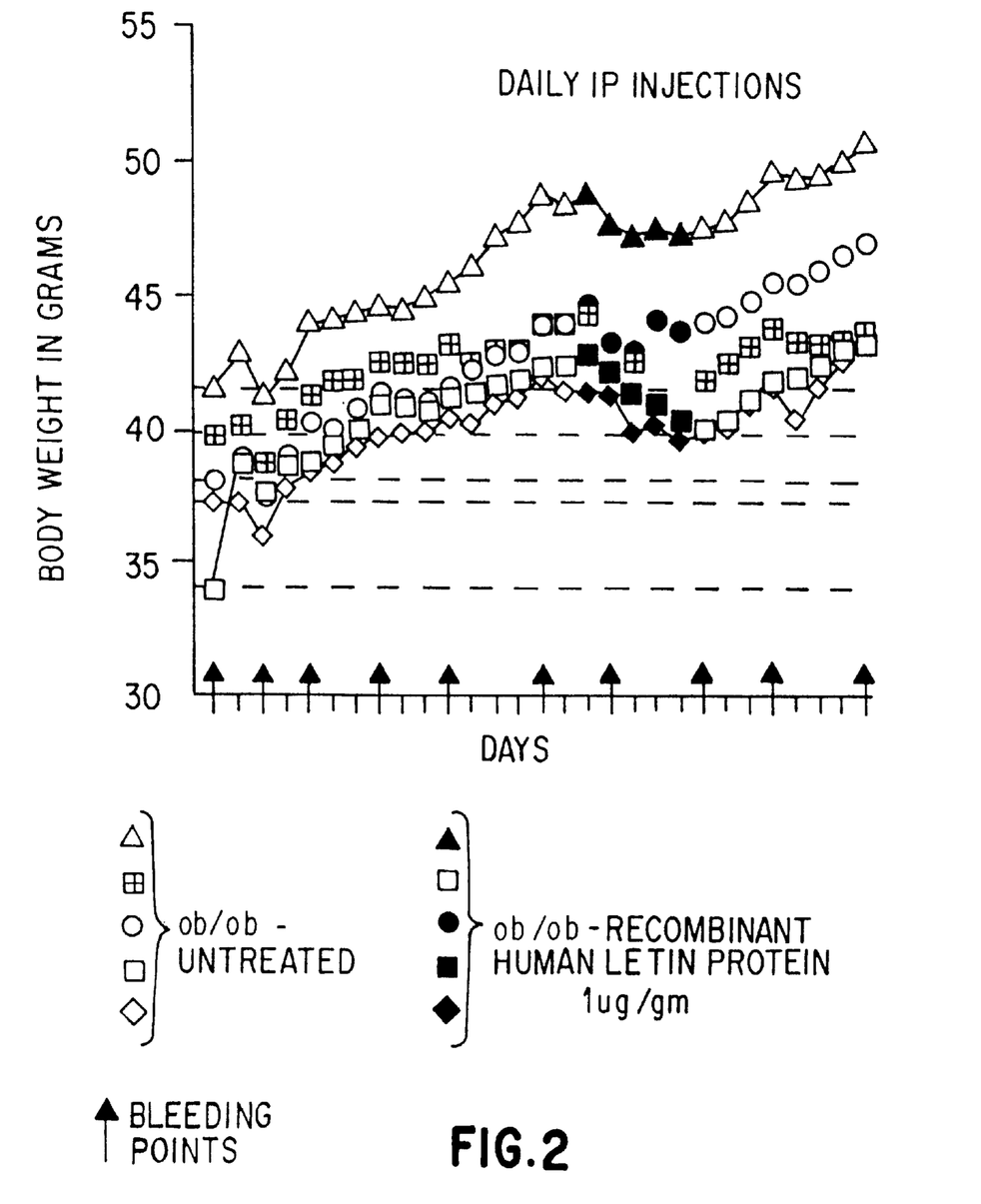
FIG. 2 is a graph showing the body weight changes of mice treated with recombinant human leptin protein. Injections of human recombinant leptin were given daily IP, at 1 µg/gm body weight. Arrows indicate bleeding points.
Figure 3:
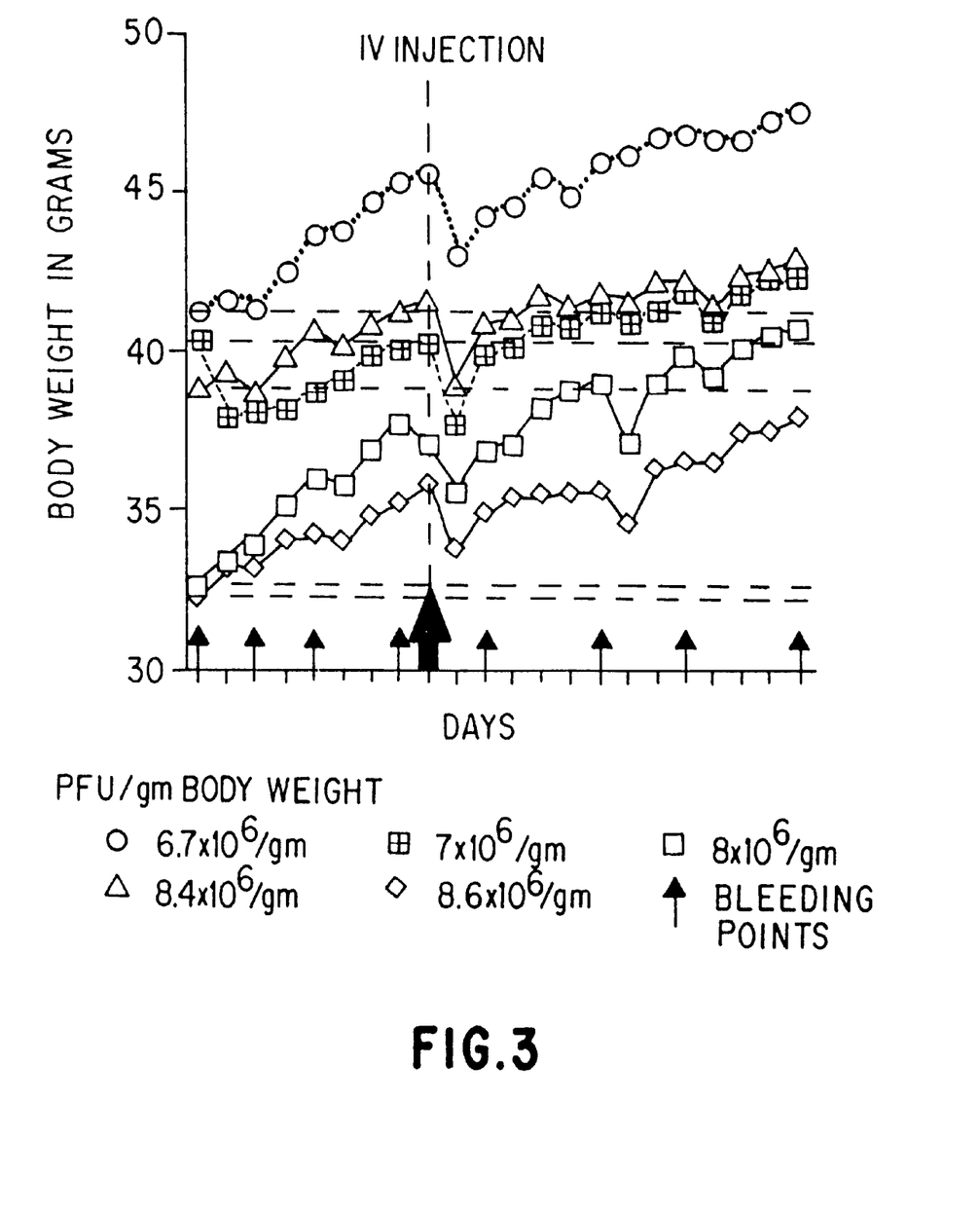
FIG. 3 is a graph showing body weight changes of mice treated with adenovirus carrying a reporter gene (β-galactosidase), used as a control.
Figure 4:
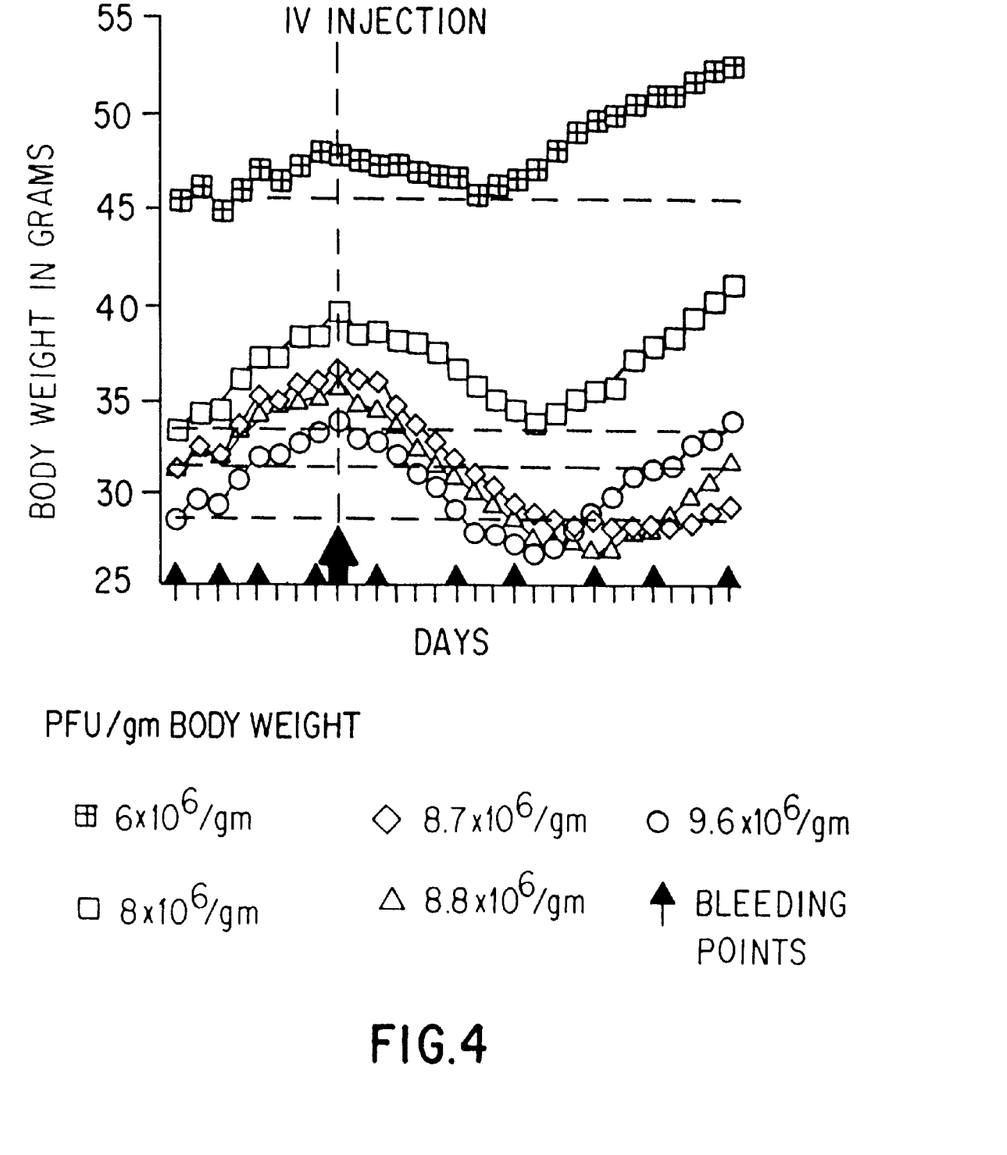
FIG. 4 is a graph showing body weight changes of mice treated with adenovirus carrying the human leptin gene.

Body-weight: FIG. 2 illustrates the body weight changes for mice receiving 1 μg/gm body weight human recombinant leptin protein injections daily, compared to untreated controls. Animals receiving leptin were injected for five consecutive days, shown by the darkened symbols on the graph. All the animals receiving the leptin lost weight within 24 hours post-injection. All animals gain weight within 48 hours after the last IP injection. FIG. 3 illustrates the weight measured for mice receiving various titers of an adenovirus carrying the reporter gene. All animals continued to gain weight post injection. FIG. 4 shows the results for mice receiving an adenovirus carrying the leptin gene. As can be seen from the graph, all animals lost weight within 24 hours post injection. They continued to loose weight for 1–2 weeks post treatment. The injections were effective over a relatively large titer range, and a dose-effect was noted.

Figure 5:
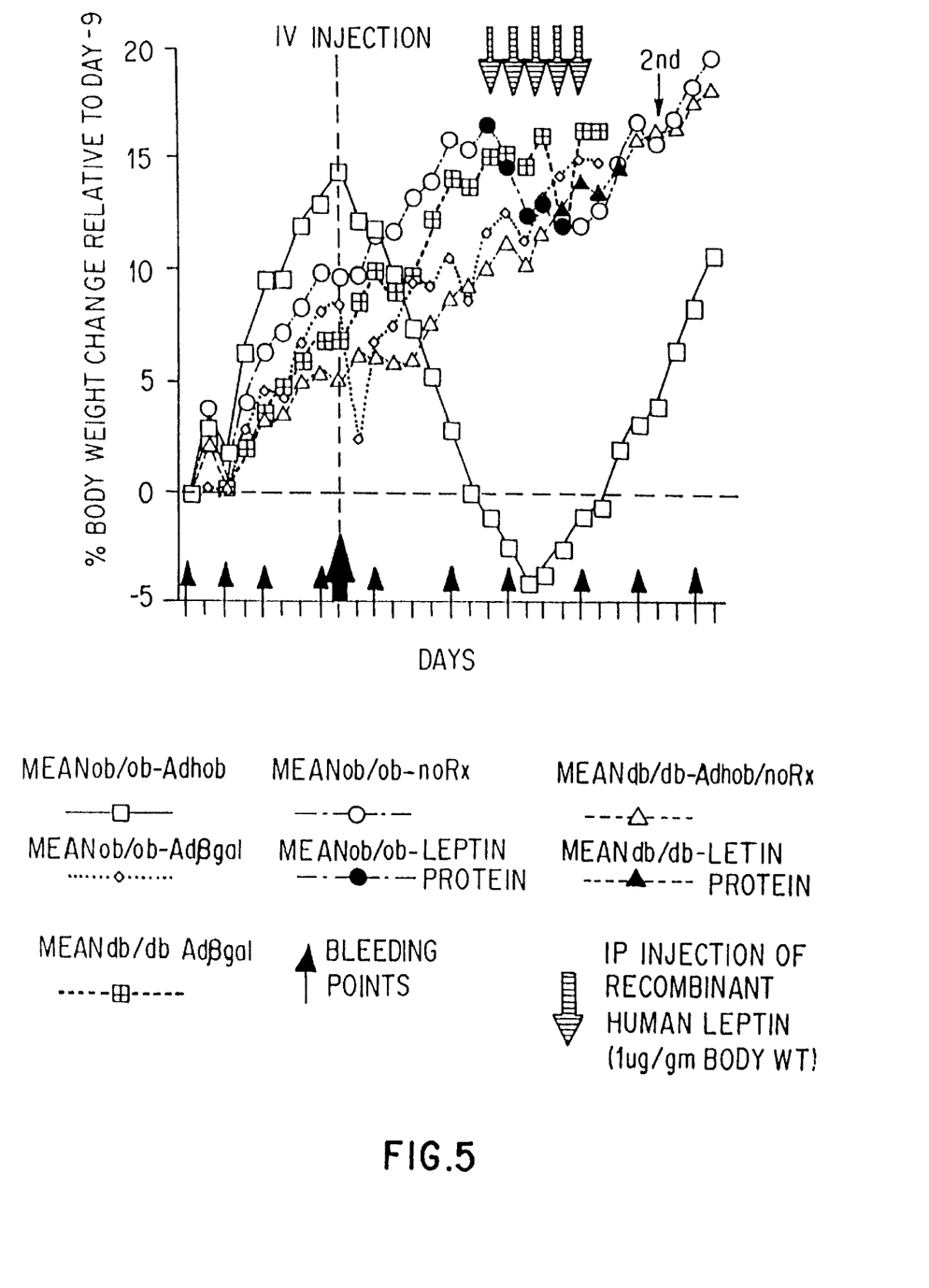
FIG. 5 is a graph showing the percent of body weight changes for all groups of mice.

Along with absolute changes in weight, the percentage body weight change was calculated for all groups. In the animals treated with recombinant leptin injections, weight loss plateaued at day three, and from day 1–5 post treatment, a 4.7% loss in body weight was noted. In those mice treated with the vector carrying the leptin gene, weight loss persisted over a 10–12 day period, and resulted in an 18.61% loss in body weight. Furthermore, over days 1–5 post treatment, a 9.17% loss in body weight was observed compared to only 4.7% loss in the recombinant leptin treated mice. This is illustrated in FIG. 5.

Figure 6A:
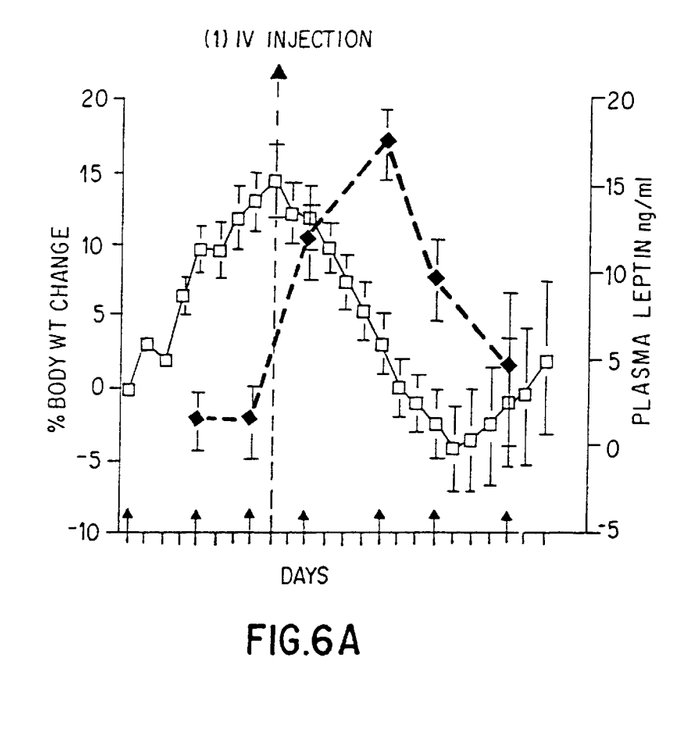
FIG. 6A (left graph) is a graph showing the amount of human leptin found in the plasma of mice treated with adenovirus containing the leptin gene.
Figure 6B:
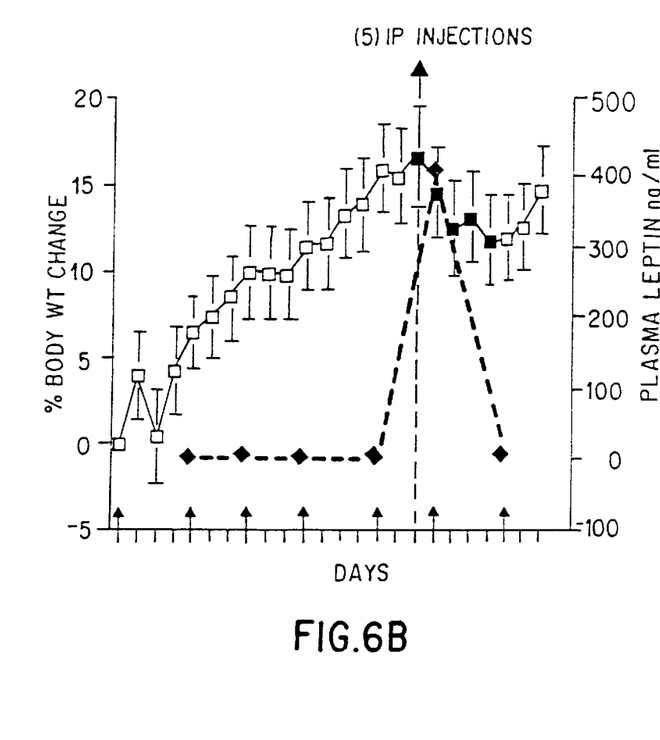
FIG. 6B (right graph) shows results for mice treated with five daily injections of recombinant human leptin.

Leptin: The amount of human leptin in plasma was measured in the animals which received injections of human recombinant leptin and those which received the vector carrying the leptin gene. Those receiving the recombinant protein were noted to have leptin levels which were approximately 20-fold higher than the amount of leptin found in control (lean, wild type) animals; peak amounts of 399.8±40.91 ng/ml. Those receiving the leptin gene had levels of leptin in their plasma which was within the normal range found in a wild-type mouse (17.52±4.66 ng/ml). In both groups of animals, weight gain was synchronized with the fall of human leptin detected in the plasma. This is illustrated in FIG. 6.

Figure 7A:
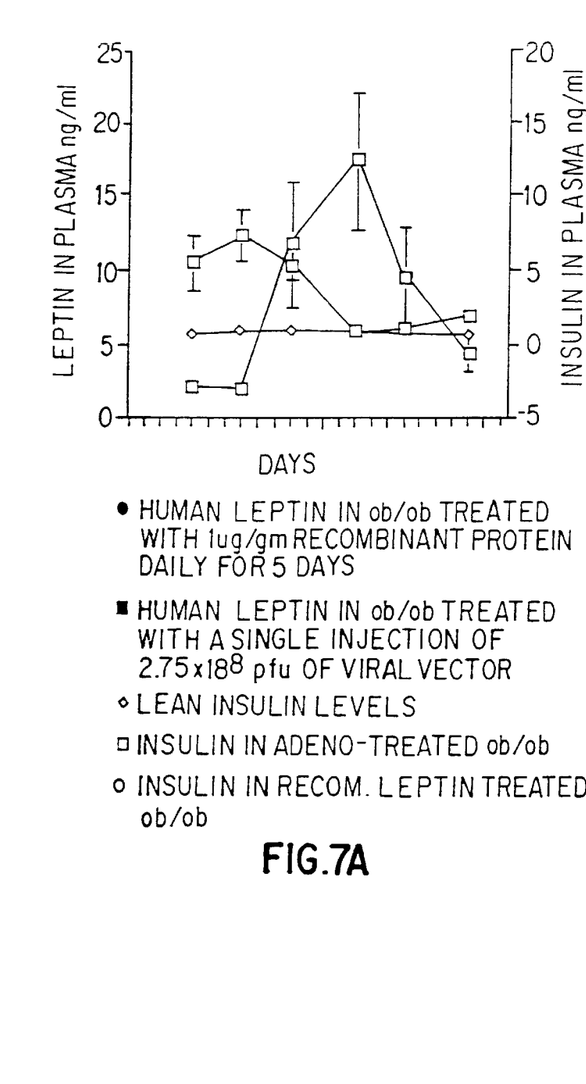
FIG. 7A (left graph) shows the amount of insulin and leptin in plasma of mice treated with adenovirus containing the leptin gene.
Figure 7B:
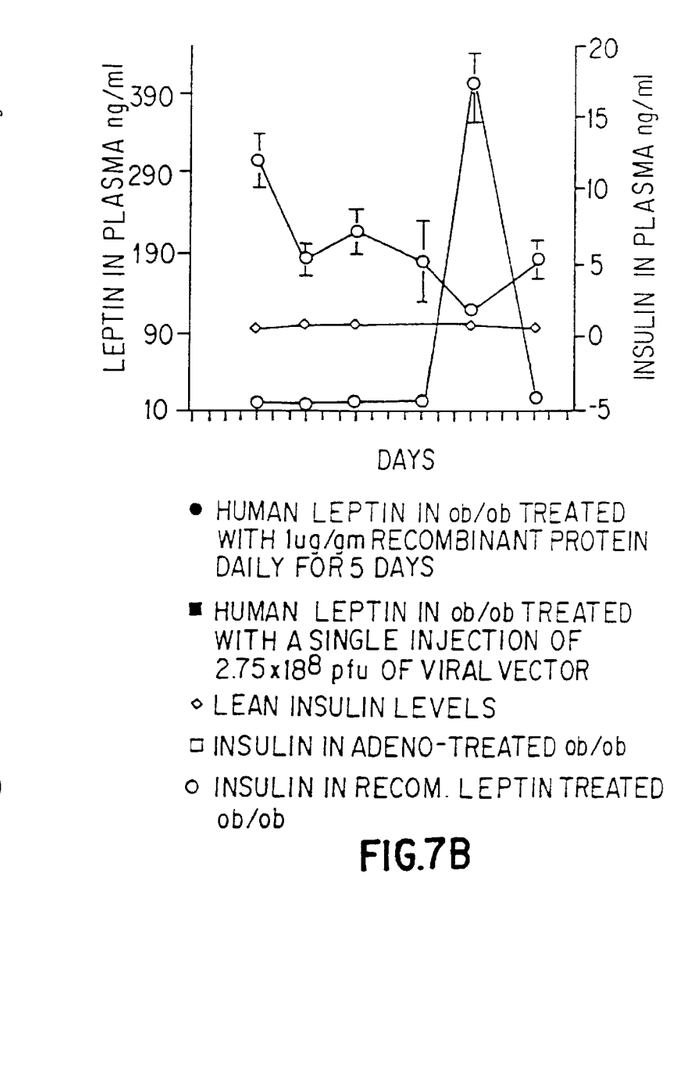
FIG. 7B (right graph) shows the amount of insulin and leptin in plasma of mice treated with recombinant human leptin injections.

Insulin: The amount of insulin in the plasma was measured in both the animals receiving recombinant protein and those which received the gene therapy. This is illustrated in FIG. 7. In both groups, insulin levels were observed to drop to those found in lean (wild-type) levels and was inversely correlated to leptin levels. In the mice receiving gene therapy, the low insulin levels were sustained for at least one week whereas in the recombinant leptin-treated mice, insulin levels increased to pre-treatment levels within 24 hours post injection.

Figure 8:
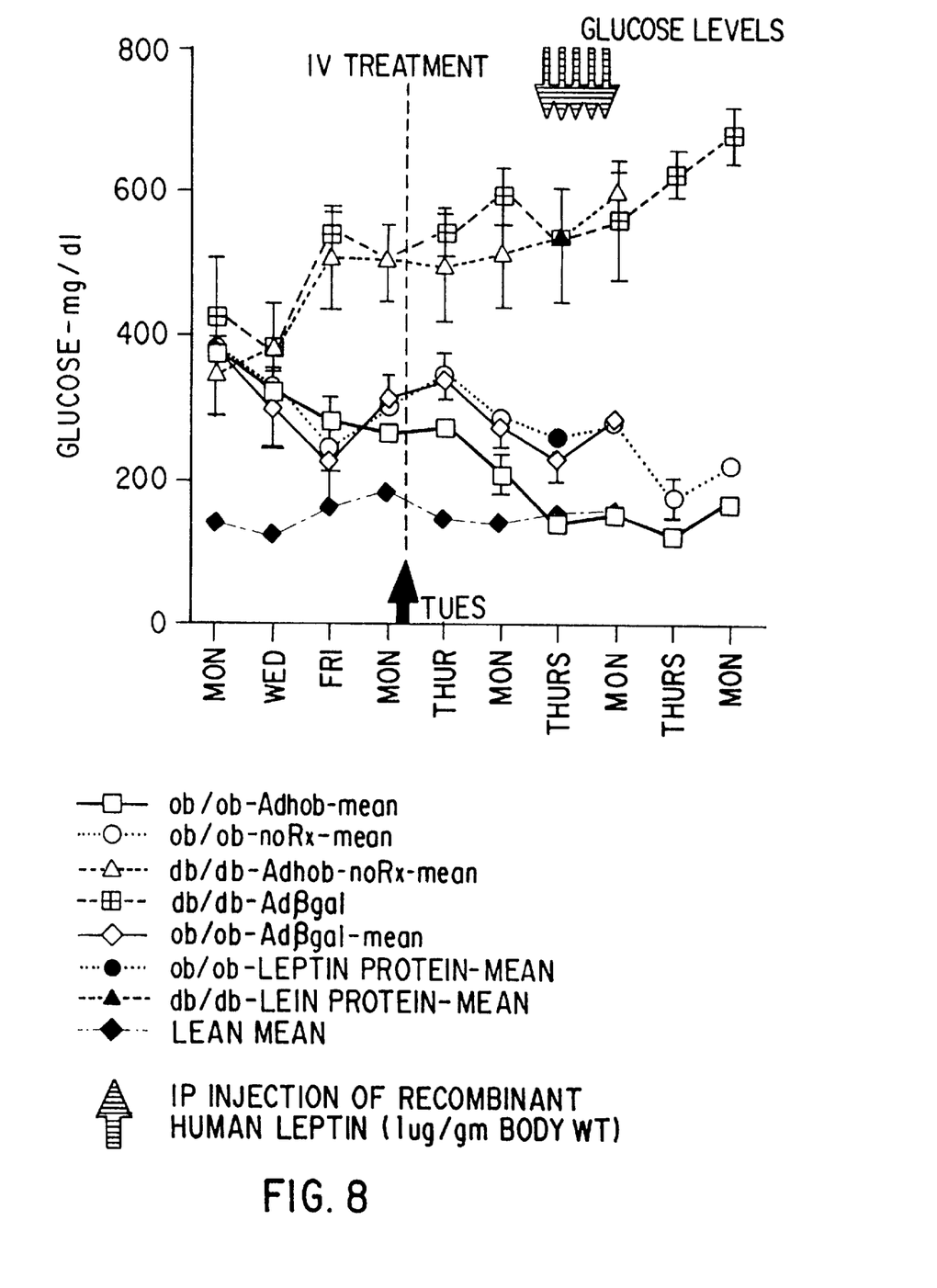
FIG. 8 shows glucose levels of the mice treated with either recombinant leptin, reporter gene or adenovirus containing the leptin gene.

Glucose: The levels of glucose in plasma was also measured in mice receiving recombinant leptin and those receiving the gene therapy treatment. In both groups, the glucose levels dropped within 6–9 days post treatment. The recombinant protein-treated mice did not achieve levels comparable to those found in lean, wild-type mice, and only sustained the lower level for less than one week. On the other hand, the mice which received the gene therapy had reductions in glucose levels to that of wild type lean mice, and they sustained this reduced level for at least two weeks. This is illustrated in FIG. 8.

The following non-limiting Examples are presented to better illustrate the invention.

EXAMPLE 1

Cloning and expression of leptin

Two PCR cDNA amplification fragments were obtained from Jefferson University (generated by cloning both variants from a Clontech phage human hypothalamic library): one coding for the human leptin and one for the human leptin variant with glutamine, (Zhang et al., 1994, *Nature* 372:425; Considine et al., 1995 *J. Clin. Invest.* 95:2986). Both PCR fragments were amplified for cloning purposes. Two primers were designed and ordered from GIBCO BRL Custom Primers:

Forward primer: ATG CAT TGG GGA ACC CTG TG

Reverse primer: TCA GCA CCC AGG GCT GAG GT

The primers were used to re-amplify the cDNA as follows: 2 μl each primer (0.3 μg/μl stock), 2 μl dNTP (10 μM, Pharmacia), 10 μl 10×PCR Buffer (Buffer 2 from Expand Long Template PCR System Kit, Boehringer Mannheim), 2 μl Taq polymerase (Perkin Elmer), 3 μl template DNA and 18 μl water. PCR cycling conditions were as follows: Mixture was incubated at 94° C. initially (without the addition of the Taq enzyme) for 1–2 minute, Taq was then added to each tube and the cycling program was initiated, 20 cycles of 94° C. for 30 seconds, 45° C. for 45 seconds and 72° C. for 1 minute. At the end of the 20 rounds of amplification the samples were incubated at 72° C. for 7 minutes. The expected fragment size in each case (human leptin-hOb, and human leptin with glutamine-hOb$_{GLN}$) was 501 and 504, respectively. The PCR amplified fragments were cloned into pCR-Script SK(+) plasmid (Stratagene) and several selected bacterial colonies were grown, plasmids extracted and sequenced to verify correct sequence of both cloned.

Inserts were then used for generating recombinant adenoviral shuttle vectors. The adenoviral vectors used in this study are essentially the same as those described in Morsey et al 1993 *J. Clin. Invest.* 92: 1580–86, which is hereby incorporated by reference, except for the leptin gene insert. The pdelE1sp1CMV-BGHpA adenoviral shuttle vector, obtained from Baylor College of Medicine was used for the cloning of the two inserts (hOb and hOb$_{GLN}$) Similarly mOb cDNA (Zhang et al., 1994 *Nature* 372:425) was inserted into pdelE1sp1CMV-BGHpA. All three shuttles (pdelE1sp1CMV-mOb-BGHpA, pdelE1sp1CMV-hOb-BGHpA and pdelE1sp1CMV-hOb$_{GLN}$-BGHpA) were tested for leptin expression by western blot analysis.

EXAMPLE 2

The three shuttle vectors from the previous example are used in rescue replication of the deficient El deleted adenoviral vectors. 293 cells, commercially available from Microbix, passage 27–30 were set up one day ahead of transfection in 60mm dishes, and were about 70–80% confluent at the time of use.

Plates were made containing one of the shuttle plasmids and pJM17; pFG140 (purchased from Microbix Biosystems Inc.) was used as a positive control for the efficiency of transfection. Plaques were identified, and plugged out of the agarose overlay using a sterile glass Pasteur pipette. Each plugged plaque was resuspended in 100–500 µl of PBS (with calcium and magnesium) in 10% glycerol, frozen at −80° C. and thawed (1–3 times). The thawed plaque was then used to infect a 90% confluent 6 cm plate of 293 cells to expand the isolated virus. 5–8 days post infection, cytopathic effects (cpe) were apparent on the cells (cells rounded up and started to detach and float in media). Cells were collected by scraping and tested for leptin expression by western analysis and for DNA restriction pattern by Hind III digestion of extracted DNA and ethiduim bromide stained gel analysis. One of the positive plaques identified based on leptin secretion and correct DNA restriction pattern was selected and used for a second plaque purification followed by a similar procedure of expansion and analysis. After the second plaque purification, the virus was propagated on a large scale. Cesium banding and titration was used to purify and quantitate.

The resulting titered viral stocks (Ad-HCMV-mOb-BGH$^{PA}$, Ad-HCMV-hOb-BGH$^{PA}$ and Ad-HCMV-hOb$_{GLN}$-BGH$^{PA}$) were stored at −80° C. until use.

EXAMPLE 3

Transgenic mice

Baseline determinations Three groups of mice were used: ob/ob, db/db, and lean (wild type, controls). All groups of mice were fed milled rodent chow (5008) starting from day of arrival or day after arrival. Food consumption was also measured. After approximately 4 days on milled chow, the mice were weighed and bled for determination of plasma levels of glucose and insulin. Injections were started 8 days after the initiation of base line measurements but before injections, mice were weighed and blood samples were obtained from all study mice for determination of plasma glucose and insulin. Leptin level in plasma were also measured.

Mice were housed 5 per cage and fed milled Purina Chow 5008 in feed cups with lids. 24 hour food consumption was measured at the same time each day. Only after food consumption was equilibrated to a fairly constant level, usually 20–25 grams chow/5 mice-day, was virus injected.

On the day of injection but before injection, food consumption, body weight, and a baseline blood sample were taken in the morning from a snipped end of tail. Blood was collected into heparinized capillary tube (total volume approximately 70–100 µl). Hematocrit was measured, and plasma was collected.

Mice were injected as follows:

A. ob/ob mouse groups: iv injections, 5 mice/group

Group 1 received 2.75×10$^8$/gm wt of AdHCMV-hob-BGH$^{PA}$ (in 500 µl dialysis buffer) in the tail vein.

Group 2 received 2.75×10$^8$/gm wt of AdHCMV-βgal reporter (in 500 µl dialysis buffer) in tail vein.

Group 3 received 500 µl dialysis buffer in tail vein.

Group 4 received 1 mg/kg wt active leptin daily IP injections for 5 days.

B. db/db mouse groups: iv injections, 5 mice/group

Group 1 received 2.75×10$^8$/gm wt of AdHCMV-hob-BGH$^{PA}$ (in 500 µl dialysis buffer) in the tail vein.

Group 2 received 2.75×10$^8$/gm wt of AdHCMV-βgal reporter (in 500 µl dialysis buffer) in tail vein.

Group 3 received 1 mg/kg wt active leptin daily IP injections for 5 days.

C. Lean control mouse group: one cage of 5 mice as measure of lean parameters

No injections.

EXAMPLE 4

Leptin receptor

Adenovirus vectors are made similarly to those described in Examples 2-3, except that the leptin receptor gene replaces the leptin gene. Mice which are db/db are used in place of the ob/ob mice. Results for the db/db mice are similar to those observed with the ob/ob mice reported herein. After injection, glucose levels fall, insulin levels fall and the mice loose weight. No effect is observed in control mice and in ob/ob mice injected with vector carrying a leptin receptor gene.

DETAILED DESCRIPTION OF THE INVENTION

Not Applicable

---

What is claimed:

1. A method of treating obesity in a mammal having a deficiency in functional leptin comprising administering intravenously to the mammal an adenoviral vector comprising a DNA sequence encoding a leptin operably linked to a promoter and expressing the DNA sequence, wherein the mammal exhibits a decrease in body weight, a decrease in serum glucose levels and/or a decrease in serum insulin levels.

2. A method according to claim 1 wherein the adenoviral vector is expressed in liver.

3. A method according to claim 1 wherein the mammal is a human.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: PCR primer

<400> SEQUENCE: 1
atgcattggg gaaccctgtg                                          20
```

```
<210> SEQ ID NO 2
<211> LENGTH: 20
<212> TYPE: DNA
<213> ORGANISM: Artificial Sequence
<220> FEATURE:
<223> OTHER INFORMATION: PCR primer

<400> SEQUENCE: 2
tcagcaccca gggctgaggt                                               20
```